(12) United States Patent
Luthje et al.

(10) Patent No.: US 7,073,390 B2
(45) Date of Patent: Jul. 11, 2006

(54) SENSOR FOR DETERMINING THE STATE OF PARAMETERS ON MECHANICAL COMPONENTS WHILE USING AMORPHOUS CARBON LAYERS HAVING PIEZORESISTIVE PROPERTIES

(75) Inventors: Holger Luthje, Halstenbek (DE); Jochen Brand, Braunschweig (DE)

(73) Assignee: Fraunhofer-Gesellschaft zur Forderung der angewandten Froschung e.V. (DE)

( * ) Notice: Subject to any disclaimer, the term of this patent is extended or adjusted under 35 U.S.C. 154(b) by 133 days.

(21) Appl. No.: 10/168,293

(22) PCT Filed: Jan. 8, 2001

(86) PCT No.: PCT/EP01/00147

§ 371 (c)(1),
(2), (4) Date: Oct. 21, 2002

(87) PCT Pub. No.: WO02/05403

PCT Pub. Date: Jun. 11, 2002

(65) Prior Publication Data

US 2003/0089177 A1 May 15, 2003

(51) Int. Cl.
*G01B 7/16* (2006.01)

(52) U.S. Cl. ............... 73/777; 310/358; 252/62.9 R
(58) Field of Classification Search ............ 73/777; 264/401; 310/358; 324/543; 252/62.9 R
See application file for complete search history.

(56) References Cited

U.S. PATENT DOCUMENTS

| 6,180,049 B1 * | 1/2001 | Jang et al. ............... 264/401 |
| 6,271,621 B1 * | 8/2001 | Ito et al. ..................... 310/358 |
| 6,534,999 B1 * | 3/2003 | Brown ........................ 324/543 |

FOREIGN PATENT DOCUMENTS

| DE | 693 11 479 T2 | 9/1993 |
| DE | 44 19 009 A1 | 5/1994 |
| DE | 44 19 393 A1 | 5/1994 |
| DE | 197 22 728 A1 | 5/1997 |
| EP | 0 087 836 A1 | 2/1983 |
| EP | 0 685 297 A1 | 5/1995 |
| EP | 0 844 469 A | 5/1998 |
| EP | 1 057 586 A | 12/2000 |
| WO | WO87/04236 | 7/1987 |

OTHER PUBLICATIONS

Angus, John C. and Wang, Yaxin; "Diamond–Like Hydrocarbon and Carbon Films," Diamond and Diamond–Like Films and Coatings; Series B: Physics vol. 266, Plenum Press, New York 1991, pp. 173–177.

Devenyi, A., et al., "Electrical transport and structure of vacuum deposited carbon films," Proceedings of the International Conference on the Physics and Chemistry of Semiconductor heterojunction and layer structures, IV (1971) p. 97–104.

Grigorovici, R., et al., "Properties of Amorphous Carbon Films," Journal of Non–Crystalline Solids 8–10 (1972), 793–797, North–Holland Publishing Co.

Devenyi, A., et al., "Electrical Transport in Amorphous Carbon Films," 2nd International conference on conduction in low mobility materials. (1971) p. 217–28.

* cited by examiner

*Primary Examiner*—Michael Cygan
*Assistant Examiner*—Jewel V. Thompson
(74) *Attorney, Agent, or Firm*—Salter & Michaelson

(57) ABSTRACT

The present invention relates to a sensor for measuring actual loads acting upon a surface of a mechanical component, wherein as a sensor an amorphous hydrocarbon layer with piezoresistive properties is used, which is preferably doped with at least one metallic and/or non-metallic element and is connected by contacts to a measuring device; the present invention further relates to the use of carbon layers having piezoresistive properties and preferably doped with metallic and/or non-metallic elements as a sensor for load measurements, as well as to a method of measuring actual loads at stressed surfaces of mechanical components, wherein as a measuring sensor an amorphous carbon layer preferably doped with metallic and/or non-metallic elements is used.

19 Claims, 9 Drawing Sheets

Figure 1:
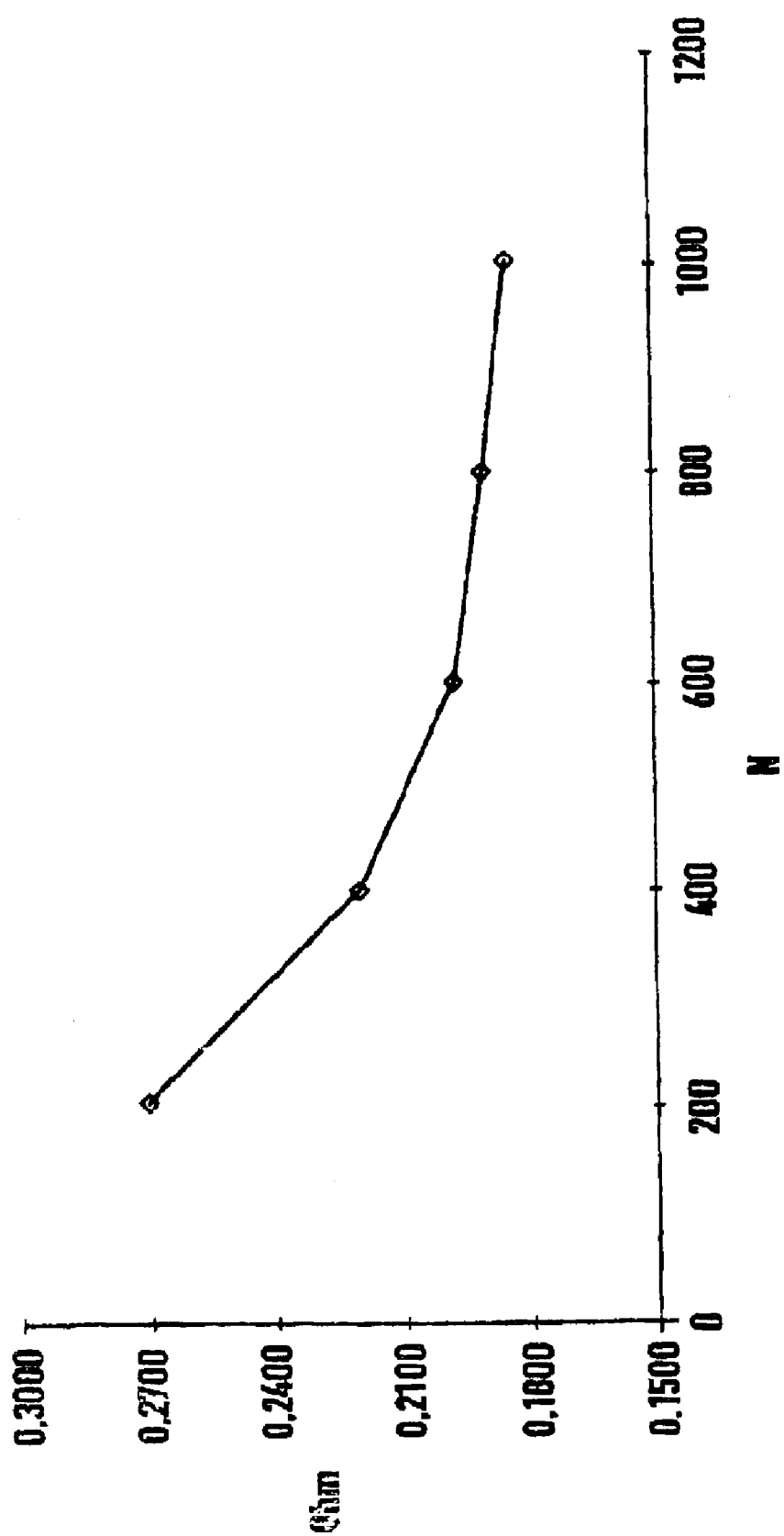

SENSOR FOR DETERMINING THE STATE OF PARAMETERS ON MECHANICAL COMPONENTS WHILE USING AMORPHOUS CARBON LAYERS HAVING PIEZORESISTIVE PROPERTIES

The present invention relates quite generally to a measuring methodology for determining state variables such as pressure, force and load of mechanical components such as e.g. machine components and tools, using amorphous carbon layers with piezoresistive properties.

The knowledge and observation of the actual state of stressed or loaded surfaces of components or tools is of crucial importance for the control and optimization of machining processes.

There is therefore a need for devices and methods, by means of which in an economical and simple manner the relevant characteristic quantities (pressure, action of force etc.) may be reliably and reproducibly measured as far as possible directly at the point of origin/action and in the case of machines as far as possible during operation.

Such measuring devices for determining the actual state variables have to be sufficiently wear-resistant to withstand the high forces which may arise at the working surfaces of tools or at the loaded surfaces of machine components. Depending on the use e.g. in friction pairings, they should at the same time as the electrical functions present a low frictional resistance.

EP 0 685 297 and WO 87/04236 describe sensors for determining state variables directly at the wearing surface of reshaping and chip removing tools, i.e. at the cutting edge and/or chipping face, and at the working surfaces of a wide variety of machine components, wherein at the relevant points of the components thin-layer technology and lithographic methods are used to apply printed conductors and circuits for determining variables appropriate to the type of component, here in particular wear and temperature. The sensors described there do admittedly allow direct measurement of the state variables at the point of origin and/or also during operation of the relevant machine component although manufacture of the printed conductors and circuits entails a multistage work cycle. They also have to be protected by protective layers from wear and the high forces which arise. This applies particularly to applications where the abrasive or adhesive loads of the material are high, such as e.g. at the working surfaces of tools.

A further example of mechanical components, for which the determination of state variables is important for simplifying work, are connection elements such as screws, rivets, nuts, or washers etc. Relevant state variables here are, for example, the prestressing force for setting the correct screw initial tension or the contact pressure for establishing whether the connection element fits tightly enough and/or whether it has loosened.

In DE 44 19 009, therefore, a measuring device for measuring the prestressing force of a screw connection is described, wherein a washer is designed so as to have, in addition to the central screw hole, a radial or secant-like bore, wherein the load-dependent deformation of said second bore is measured capacitively. For correct measurement, in said case, a precisely defined second bore is crucially important.

In the apparatus according to DE 693 11 479 measurement of the contact pressure is effected via the bending of a force sensor, which is fastened to the connection element and which during a tightening operation deforms reproducibly in dependence upon the exerted force.

A need existed for a measuring methodology for determining state variables, in particular the action of force and pressure, by means of which it is possible actually to measure the respective state of the relevant surface of any desired mechanical component and which is moreover wear-resistant, has low coefficients of sliding friction and may, without extensive modification, be universally adapted to, and used for, a wide variety of applications.

According to the invention said object is achieved by a measuring methodology, which uses, as a sensor, amorphous carbon layers with piezoresistive properties.

In the context of the invention "amorphous carbon layers" may be hydrogen-free carbon layers, so-called i-carbon (i-C) layers, or alternatively carbon layers, so-called a-C:H layers and/or DLC (diamond-like carbon) layers, with or without further metallic and/or non-metallic doping elements.

So-called hard material layers of amorphous hydrocarbon, known in short as a-C:H layers or also DLC layers (diamond-like carbon), are known as such and widely described in literature (e.g. R. E. Clausing et al. "Diamant and Diamant-like Films and coatings", Plenum Press, New York, 1991). They are notable in particular for their extreme hardness, wear resistance and low coefficients of friction and are therefore widely used as wear protection coatings.

It is further known that the properties of said layers, such as the wear and adhesion characteristics or the coefficients of friction, are influenceable through the addition of further elements and may be adjusted in a defined manner for the respective application.

Thus, in EP-O-A 087 836 it is proposed to add metallic elements to said layers in order to prevent the adverse influence of relative atmospheric humidity upon the coefficients of friction.

In a totally surprising and unexpected manner it was discovered that amorphous diamant-like carbon layers, particularly when they additionally contain metallic and/or non-metallic elements, behave in a similar manner to piezoresistive materials and under load, e.g. under pressure load, demonstrate a measurable variation of the electrical resistance. Although such carbon layers are widely used as wear protection coatings, observation of the piezoresistive properties is completely new and has not been described anywhere before. With the piezoresistive properties a wide variety of further areas of application, particularly in the field of sensor technology, has opened up for such carbon layers.

With the aid of the piezoresistive properties said carbon layers may be used directly as a sensor for determining actual state variables, such as pressure or action of force, of mechanical components coated with said layers, such as e.g. the previously described machine components, tools or connection elements, without any need for further measures.

As said layers may also be applied onto surfaces of widely differing geometries, they may be used universally for a wide variety of mechanical components and in particular also for those having complicated superficial structures such as corners or edges.

Through the use of carbon layers with piezoresistive properties sensors for determining actual state variables of stressed surfaces may be created, which are universally usable without special manufacturing or adaptation measures. With such sensors direct measurement is possible also at selectively delimited surfaces even in the case of large-area applications, and local information may be obtained about the actual state of—even locally delimited—measuring surfaces. By virtue of exploiting the piezoresistive properties of said layers a completely new kind of integral sensor technology may be created.

Unlike with the known piezoresistive materials, with said carbon layers the resistance level and the pressure/ resistance characteristics may be set in a defined manner in dependence upon the nature and quantity of incorporated doping elements, preferably metal atoms.

Thus, for example, metal-free DLC layers present resistivity values of more than $10^{12}\times$cm but, by incorporating e.g. additional metallic elements, the resistivity may be reduced and may assume a value in the order of magnitude of around $10^4\times$cm.

The carbon layers used according to the invention as a sensor may be obtained by means of the known chemical or physical vapour deposition techniques, such as are widely described in literature (e.g. in EP-B-0 087 836 such a method of manufacturing metal-containing amorphous hydrocarbon layers is described in detail).

Typical layer thicknesses for the carbon layers to be used as a sensor are in the range of 10 nm–500 m, preferably of 10 nm to 20 m. It goes without saying that the layer thickness is freely selectable in accordance with the concrete application.

In principle, all metallic or non-metallic elements of the periodic system are suitable for incorporation into the carbon layers, i.e. as doping elements, provided the layers obtained present piezoresistive properties. Particularly suitable examples are Si, Ti, W, Cr, Ta, Nb, V, Zr, Hf, Mo, Pd, Ni, Co, Pb, Cu, Al as well as precious metals such as Au, Ag, Pt, Ru, wherein Si, Ti, W and Cr are particularly preferred. For the present invention the term "metallic element" also includes elements classified as semi-metals.

Examples of non-metallic doping elements are oxygen, nitrogen, argon, fluorine and hydrogen. The elements may be incorporated into the layer as single atoms, clusters or alternatively doping carbides.

By selecting the nature and concentration of the incorporated elements the resistivity of the layer thereby obtained is freely adjustable within wide limits so that, depending on the desired use, the resistance level and the pressure/ resistance characteristic may be adjusted in a defined manner. It is therefore possible to obtain piezoresistive layers with adjustable electrical properties.

In the present case, the metallic doping element is incorporated into the amorphous carbon matrix generally in the form of so-called nanoparticles, which as a rule have a size of 5 to 500 nm, wherein the spaces between the nanoparticles are approximately of the same order of magnitude. It is assumed that the conduction of current effected via said incorporated particles. Surprisingly, according to the invention it was then discovered that the resistance of said layers is dependent upon the external load such as pressure load or deformation through elongation.

Said property is not confined to the metal-containing carbon layers containing doping elements but also occurs in pure amorphous carbon layers without doping elements. It is assumed that in said case what gives rise to the piezoresistive properties is the formation of islands of a predominantly $sp^2$ character, i.e. with graphite-like bond ratios, in a carbon matrix of an $sp^3$ character, i.e. with diamond-like bond ratios.

For example, the carbon layer used according to the invention may contain carbon in a proportion of 20–99.9 atom %, preferably 20–95 atom %, hydrogen in a proportion of 0.1–35 atom %, preferably 5–35 atom %, and doping elements e.g. in a proportion of 0.01–35 atom %, preferably 1–45 atom %.

Naturally, the above-mentioned proportions may be varied upwards or downwards in accordance with the special requirements of the concrete application.

According to the invention the carbon layer may be a multilayer system of differing composition in terms of the nature and/or concentration of the components. It may take the form of a gradient layer, the structure of which varies over the layer thickness.

The concrete configuration of the carbon layer used according to the invention is not subject to any special restrictions and may be designed in accordance with the requirements of the concrete application.

Where necessary, further layers such as e.g. electrically insulating protective layers, layers for improving adhesion or layers for electrical contacting may be additionally provided.

For example, non-conducting a:C—H layers, which are doped with oxygen and silicon to increase the resistance, are also suitable as an insulating layer.

An example of this is an a:C—H layer, which additionally contains silicon and optionally oxygen. To manufacture said layers, suitable precursor materials, such as e.g. hexamethyl disiloxane, may be added to the process gas. Layers for electrical contacting may comprise metals or hard materials customary for said purpose.

Depending on the desired application, said additional layers may be applied onto the respective substrate in the same process before or after the formation of the carbon layer with piezoresistive properties.

The individual layers may take the form of discrete layers, wherein each individual layer may have a homogeneous composition over the respective layer thickness and various layers may have a different composition in terms of the nature and quantity of the components.

The layers may also take the form of gradient layers, wherein within a layer the nature and/or proportion of the components varies over the layer thickness. The configuration of the layer/layers and/or layer system may be designed freely in accordance with the application. Examples of possible further layers and the configuration of layer systems are to be found in the previously cited EP-A-0 685 297, to which for said purpose reference is made in full.

In a preferred development according to the invention, the layer system applied onto the respective substrate comprises sandwich-like multiple layers for the purposeful adjustment of electrical and mechanical properties. In said case, layers having different doping materials and concentrations may be used in an advantageous manner.

As already mentioned above, the carbon layers (i-C:H, a-C:H, Me—C:H) used according to the invention may be obtained by means of the conventional PVD or CVD methods or alternatively by combining both methods. In said case, for manufacture of the corresponding layers the doping element or the respective elements are supplied through vaporization or sputtering of a solid body or via element-containing gases.

Manufacture of the layers and/or multilayer systems may be effected e.g. in a commercially available multi-day sputtering installation or in so-called continuous installations.

Applications for the invention arise wherever measurement of a component load is of interest and high standards are demanded of the wear resistance, anti-stick property and low coefficient of friction of the surface. Examples of this are reshaping and chip removing tools, cutting and punching dies, forming and pressing tools, sliding and ball bearing arrangements, roller bearings and guides.

It is moreover advantageous for the use as a sensor that the magnitude of the resistance is dependent upon the measured current. Said effect enables a purposeful dynamic adaptation of the sensor sensitivity within a large range through corresponding adjustment of the current density.

Through laser treatment, moreover, the pressure/stress characteristics of the sensor layer may be selectively purposefully adjusted, so that locally different conductivity values may be obtained.

For use as a sensor, the hydrocarbon layers with piezoresistive properties are provided in the manner customary in sensor technology with electrical contacts and with corresponding signal processing and/or evaluation circuits.

Naturally, in combination with the hydrocarbon layer used according to the invention as a sensor it is possible to integrate in the relevant mechanical components further sensors, which are designed directly as a layer or are provided in some other manner on the mechanical component, so that a plurality of state variables may be acquired.

Thus, temperature sensors enabling thermal stabilization may be provided. The use of temperature sensors is meaningful also for taking into account and accordingly working out the influence of temperature upon the measured values obtained.

For example, the inherent march of temperature of the layer according to the invention may be used for temperature measurement. In said case, the temperature measurement is effected at points which are not loaded by the action of force and pressure.

There now follows a detailed description of the invention by way of example and with reference to drawings.

Figure 2:
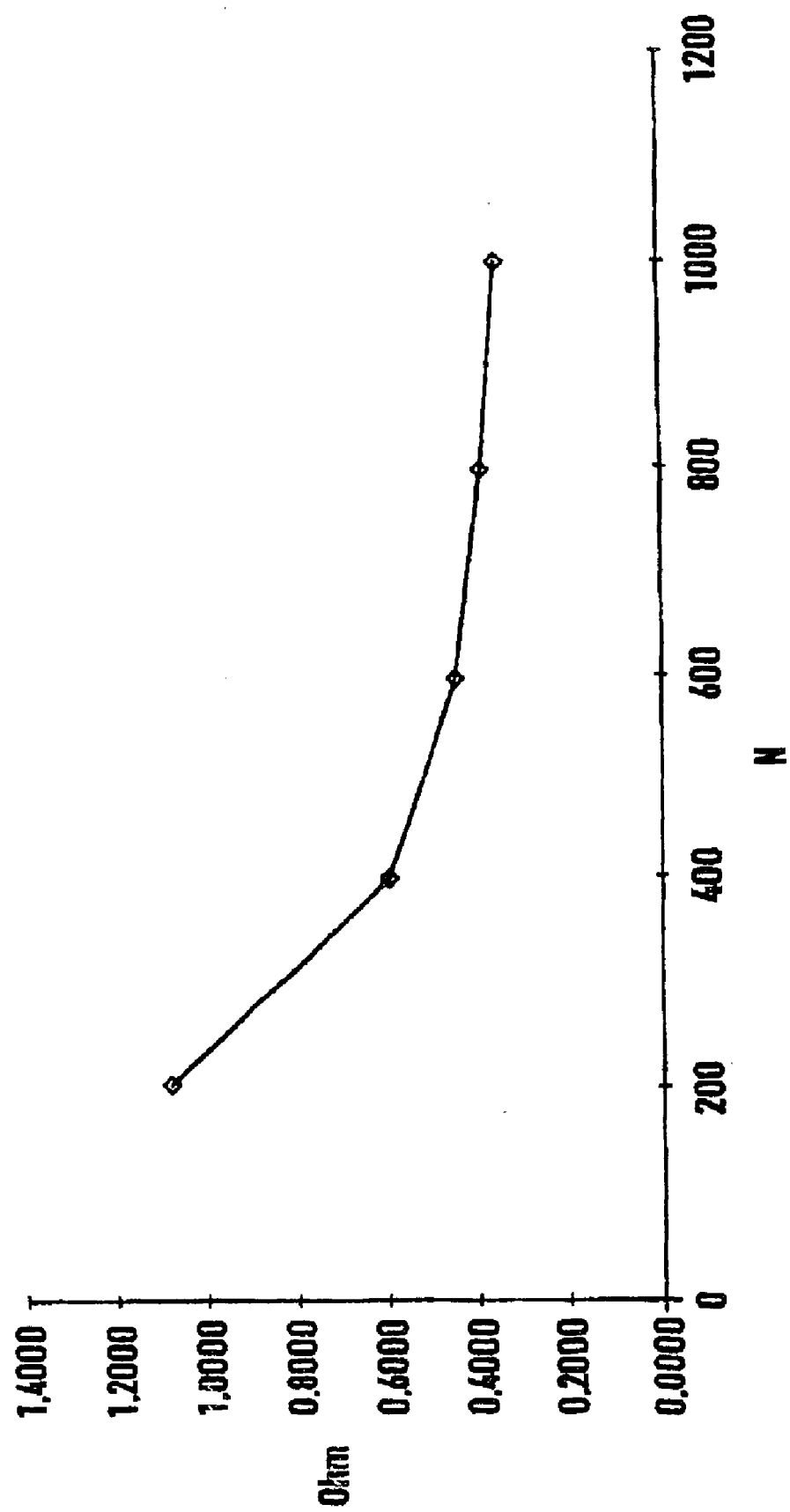
Figure 3:
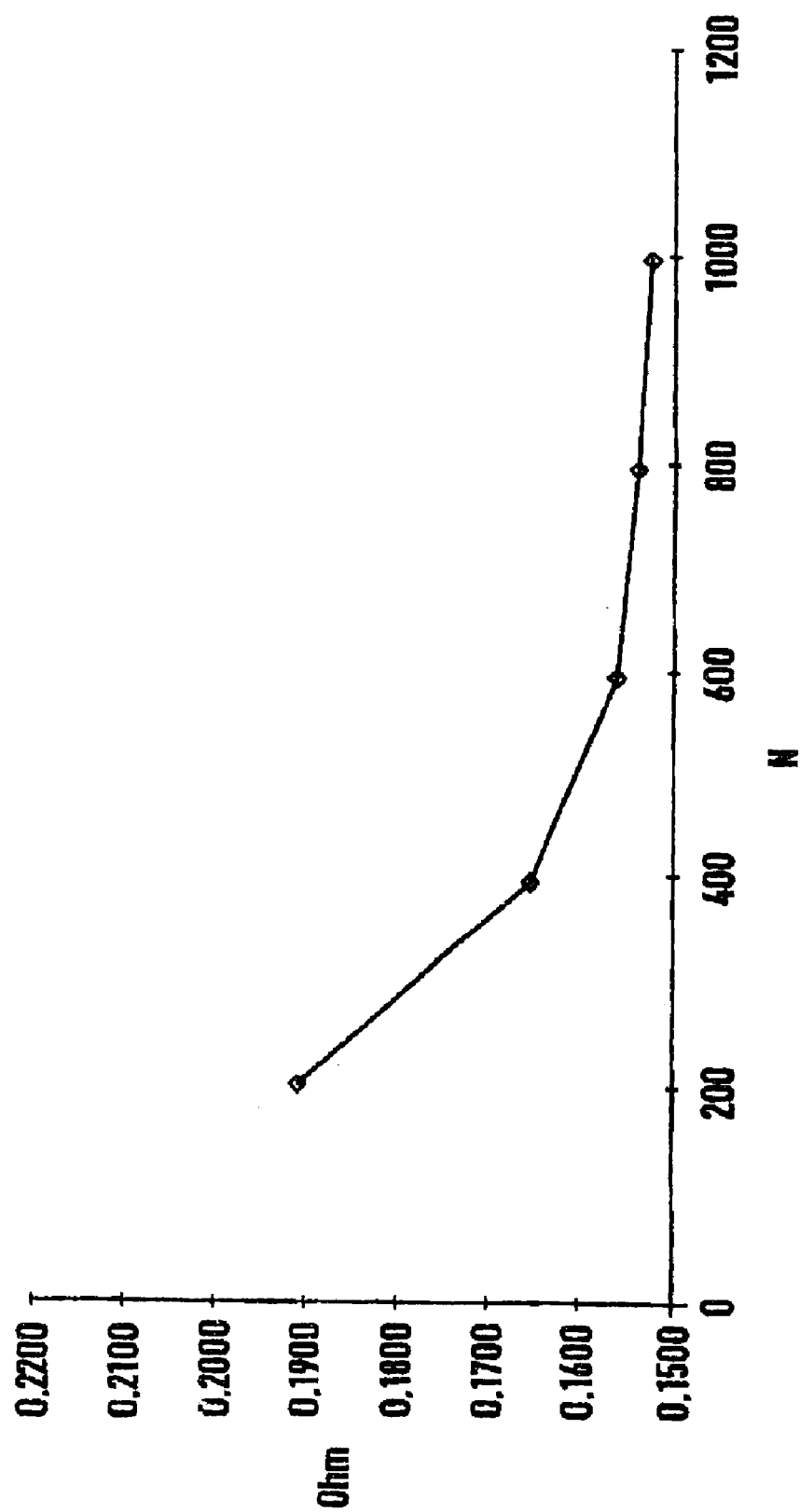
Figure 4:
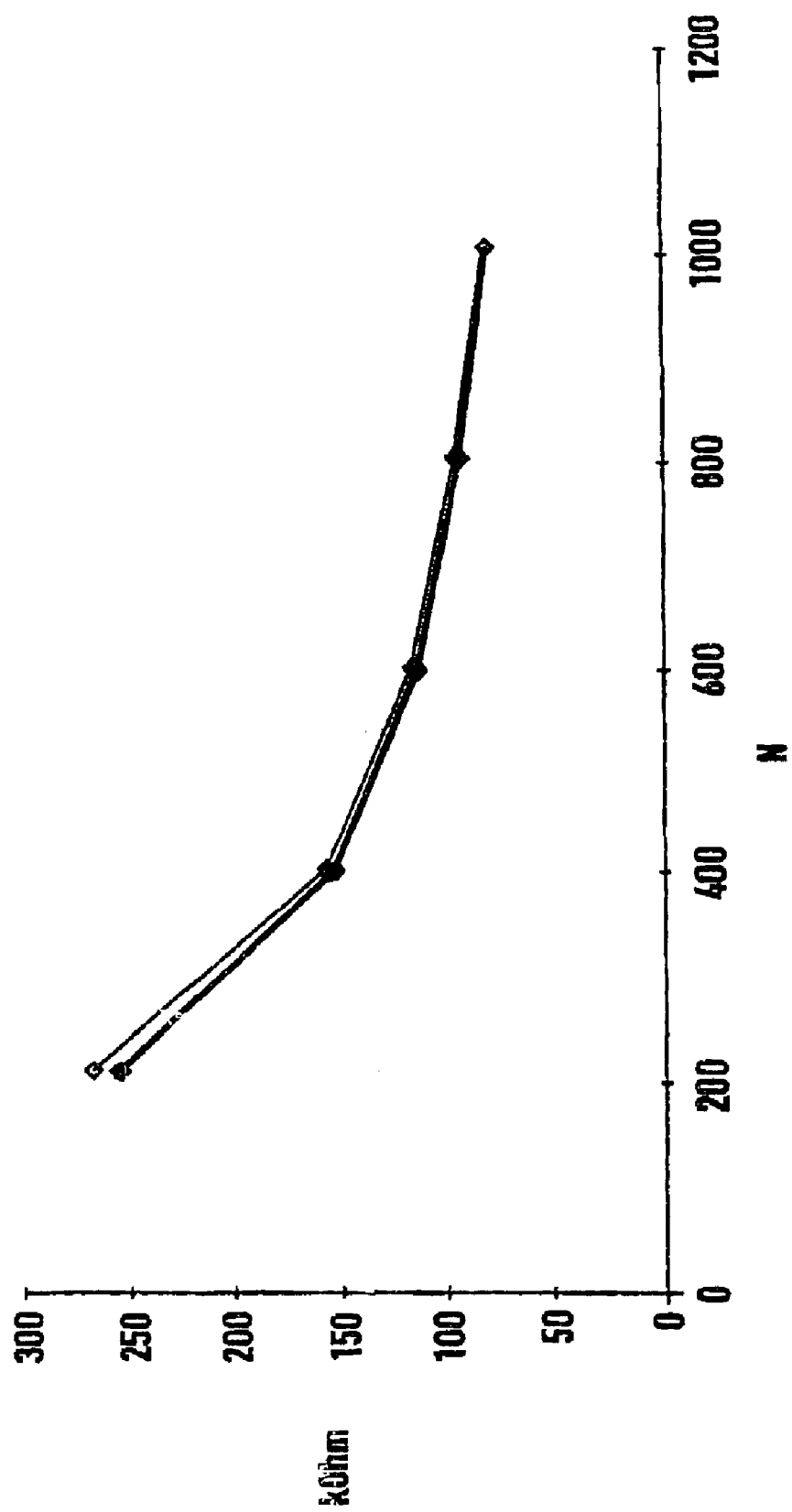

The drawings show:

FIGS. 1 to 3 the resistance variation of hydrocarbon layers doped with various metallic elements as a function of the effective force, FIG. 4 the resistance variation of hard amorphous hydrocarbon layers without doping, FIGS. 5 to 14 various concrete applications for the sensor according to the invention.

The diagrams in FIGS. 1 to 4 clearly show the resistance variation of differently doped and/or undoped hydrocarbon layers as a function of the force acting upon said layers. Plotted in each case to the right is the force in Newtons and in an upward direction the resistance in ohms, in FIG. 4 however in kOhms.

In FIGS. 1 to 4 the measurements were conducted using a cylindrical contact punch having a flat contact surface and a diameter of 1 nm.

FIGS. 1 to 2 show the resistance variation under the action of force of hard amorphous hydrocarbon layers with Au nanocrystals, wherein in FIG. 1: Au 43 atom %, C 54 atom % as well as further doping elements 3 atom %, and in FIG. 2: Au 30 atom %, C 68 atom % as well as further doping elements 2 atom %. Depending on the manufacturing method said layers contain up to 30 atom % hydrogen, which has been disregarded in the above information about the layer composition. As a substrate 100Cr6 was used.

Manufacture of the layers was effected in a diode sputtering installation having a diameter of 150 mm and equipped with an Au-target (gas: Ar 46 sccm/min; $C_2H_2$ 4 sccm/min; target output 500 W, 13.5 MHz).

FIG. 3 shows the resistance variation under the action of force of hard amorphous hydrocarbon layers with W and/or WC nanocrystals, with W 10 atom %, C 88 atom %, other doping elements 2 atom %. Depending on the manufacturing method, the layers contain up to 30 atom % hydrogen, which has been disregarded in the above information about the layer composition. As a substrate 100 Cr6 was used, the layer thickness is 2.2 m.

Manufacture was effected in a magnetron sputtering installation having 2 W-targets each being 800×190 $mm^2$ (gas: Ar 390 sccm/min; $C_2H_2$ 250 sccm/min; target output 2×6000 W, DC operation, substrate bias 100 V).

FIG. 4 shows the resistance variation of hard amorphous hydrocarbon layers without metallic doping. The layer thickness is 2 m. As a substrate 100 Cr6 was used. The conditions of manufacture were as follows: CVD) sputtering installation with vertical electrode 200×150 $mm^2$; gas: Ar 70 sccm/min, $C_2H_2$ 20 sccm/min, output: 500 W, 13.5 MHz.

FIGS. 5 to 14 show concrete forms of application of the carbon layer with piezoresistive properties used according to the invention for measuring actual state variables.

Figure 5:
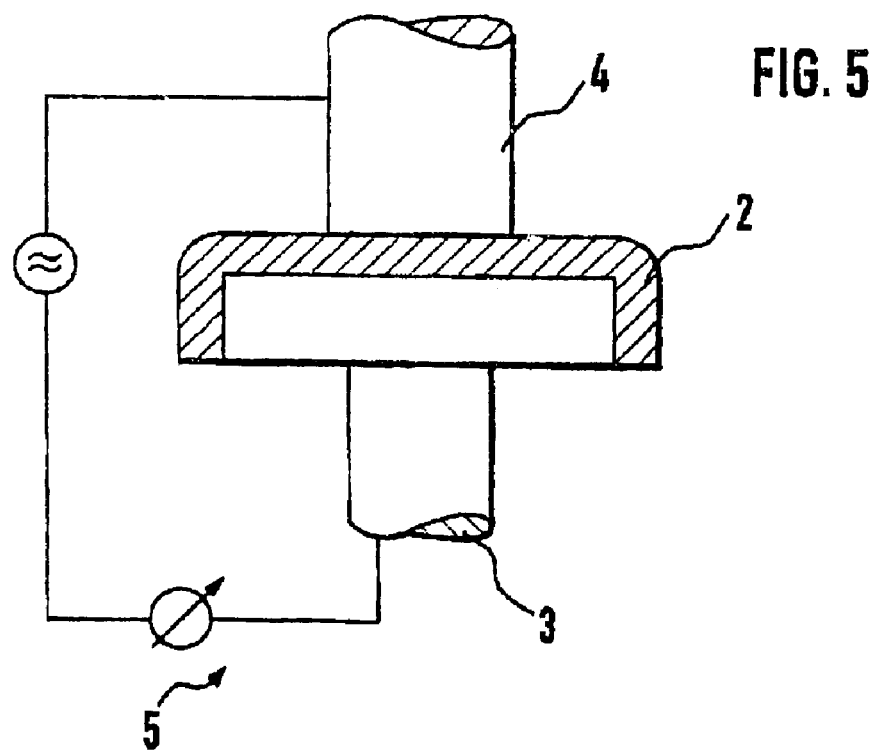

FIG. 5 illustrates the application of the layer, which is used according to the invention as a sensor, in a pressing tool, which comprises a bottom pressure ram 3, which is coated with the measuring layer 2 according to the invention, and a counterpart body 4. The material to be pressed, e.g. a metal sheet, is introduced between the counterpart body 4 and the ram 3. Said arrangement allows measurement of the actual force acting in the region of the contact surface upon the material.

Figure 6:
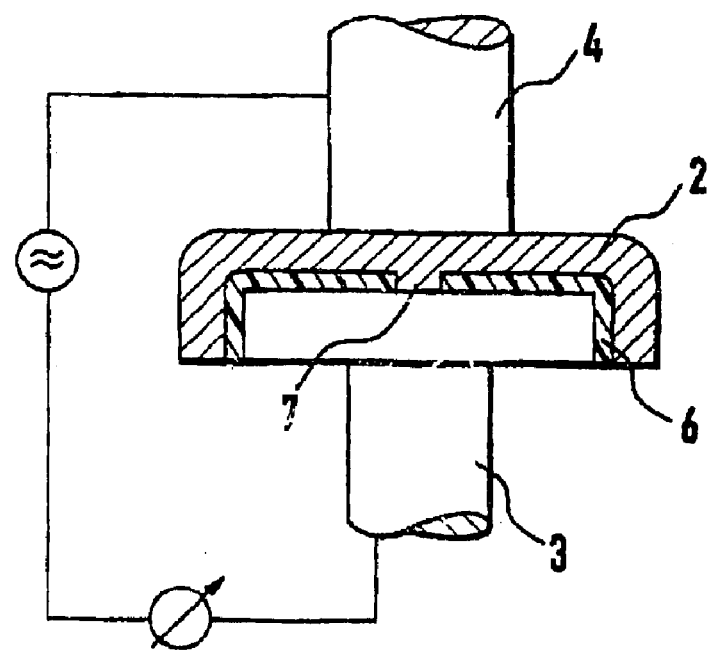

FIG. 6 shows a form of application similar to FIG. 5 only with a modified layer structure on the pressing tool, thereby enabling defined local measurements to be effected in desired zones of the tool.

In said case, the tool is first coated with a thin insulating layer 6, which is preferably stable under load, wherein by applying a mechanical mask or by means of a subsequently effected structuring a defined opening is produced as an observation window 7 in the insulating layer 6. The piezoresistive-like measuring layer 2 is then placed over the insulating layer 6. The observation window 7 allows local measurements in defined zones.

Figure 7:
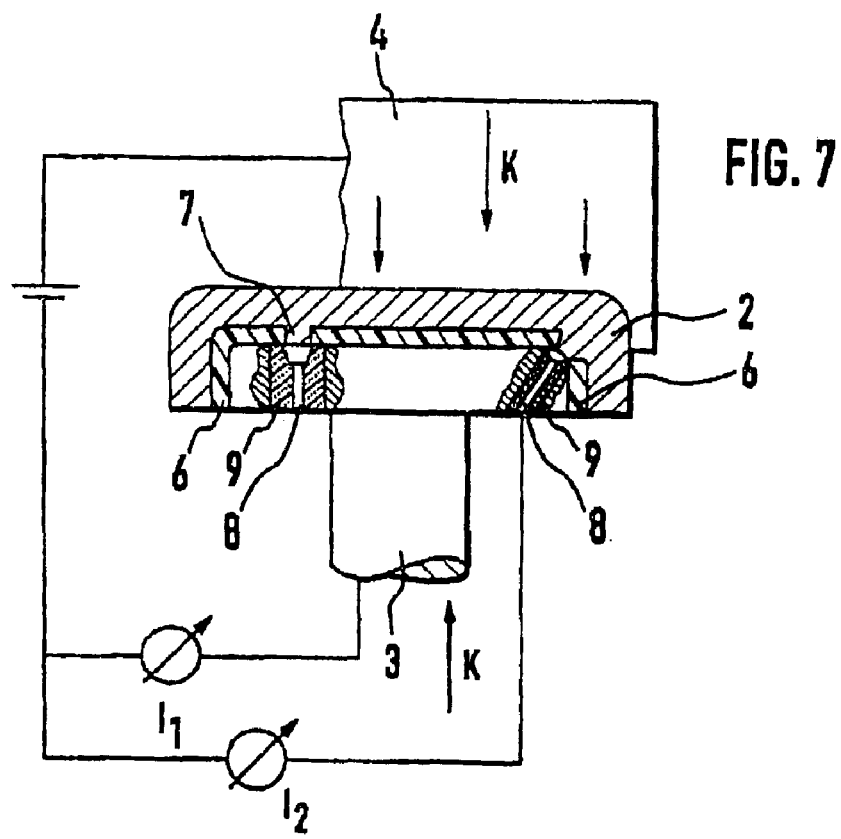

FIG. 7, like FIGS. 6 and 5, shows a pressing tool, wherein however contacts 8 are run in an insulated manner out of the pressure ram 3. Here too, there is first the formation of an insulating layer 6 with observation windows 7 and then coating with the measuring layer 2 used according to the invention. The contacts 8 are likewise surrounded by an insulating layer 9. Said form of construction allows the use of a measuring matrix with observation windows 7 as locally defined measuring points. The direction of the action of force is indicated by the arrows K.

Figure 8:
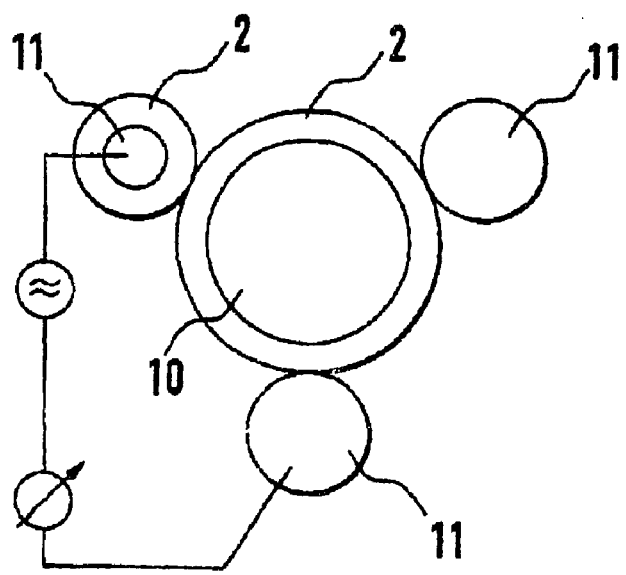

FIG. 8 shows a roller gear of the type used e.g. in the printing industry, comprising a main roller 10 and a plurality of contact pressure rollers 11. Measurement of the contact pressure is realized in that at least one of the rollers, here the main roller 10, is provided with the layer 2 according to the invention and the resistance is determined in accordance with the illustrated circuit. As is indicated in the drawing, where necessary the contact pressure rollers 11 (here, the contact pressure roller 11 top left) may be provided at the same time as the main roller 10 or independently with a measuring layer 2 used according to the invention.

Figure 9:
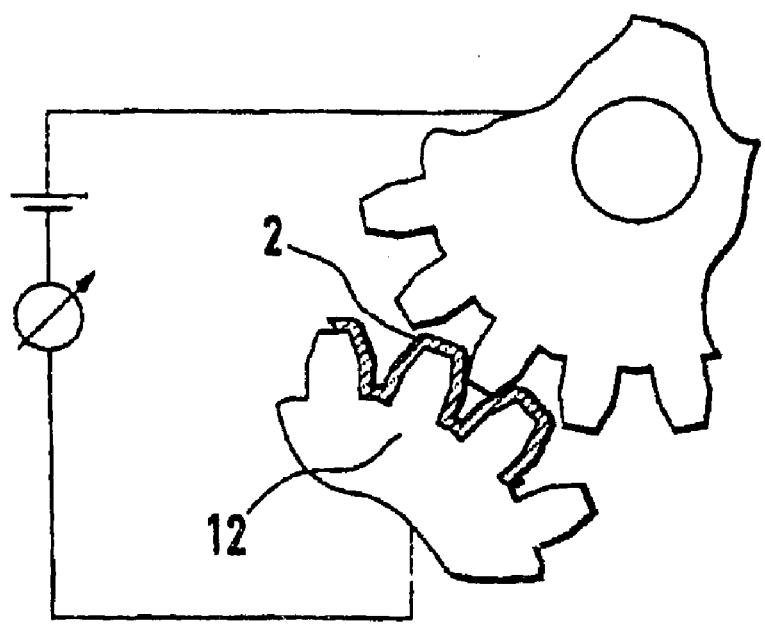

In FIG. 9 a gearwheel 12, which is provided with the measuring layer 2 used according to the invention, is diagrammatically illustrated. Here, besides performing the tribological functions the measuring layer 2 is also used to determine forces in the tooth flank region, which were previously inaccessible using other methods.

Figure 10:
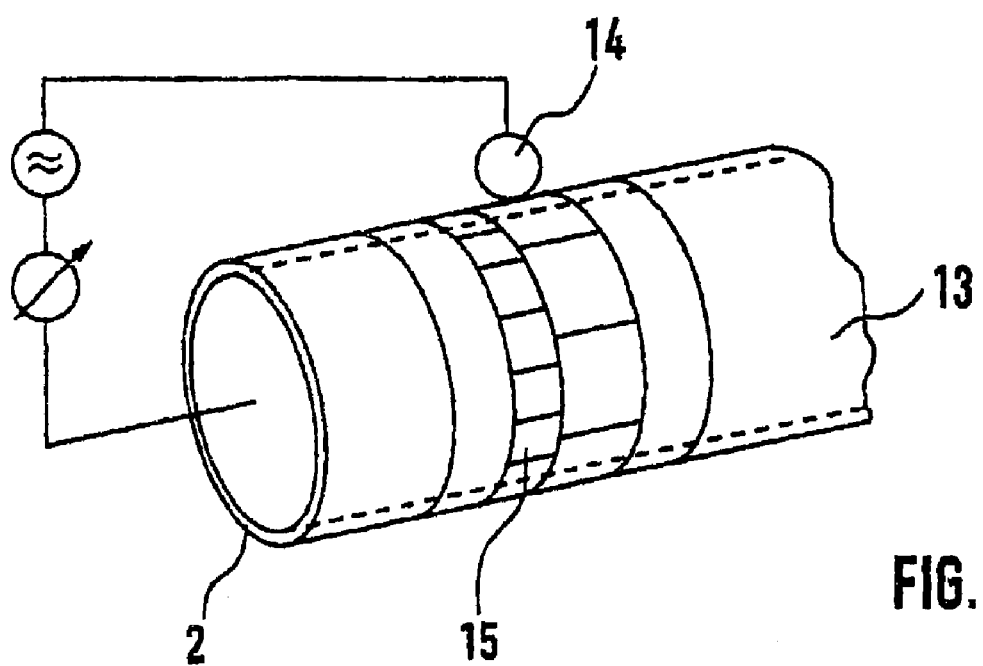

FIG. 10 shows a shaft 13, which is provided with a layer system as measuring layer 2 used according to the invention. Here, the force exerted by individual balls or rollers 14 of a bearing is to be continuously measured during operation with the aid of the measuring layer 2.

By way of said concrete example a further form of application of the carbon layer, which is used according to the invention as measuring layer 2, as a sensor for locally measuring force or other state variables at otherwise inaccessible points is illustrated. Continuous measurement in the inaccessible bearings is enabled by coating the shaft 13 firstly with a high-resistance DLC layer.

In said case, a CVD sputtering process is conducted in such a way that initially only the substrate electrode—to which the shaft 13 is fastened—is operated with an HF plasma. In said case, besides argon, $C_2H_2$ and HMDSO (hexamethyl disiloxane) are also introduced into the process chamber, After deposition of a 2 m thick DLC layer the process is modified in that, in addition to the substrate electrode, the target electrode is also acted upon by an HF plasma. The target electrode may comprise e.g. tungsten. In a preferred implementation of the process, in a first step only argon is introduced and the tungsten target is cleansed of contamination against a shutter.

During said phase a bias potential is applied to the substrate and leads to a slight etching operation.

During a second phase the shutter is opened and an approximately 50 nm thick intermediate layer of tungsten is deposited. A further phase is used to produce a gradient layer of Me:CH. To said end, a continuously increasing proportion of $C_2H_2$ is added to the argon sputtering gas. Said intermediate layer is approximately 300 nm thick. After the ultimate pressure is reached, the $C_2H_2$ flow is held constant and an approximately 1 m thick W:CH layer is deposited, which contains around 30 atom % W.

Said layer is structured, as is indicated in FIG. 10 by the reference character 15. Known photolithographic or laser-based structuring methods may be used for said purpose. In said case, defined measuring zones in the form of observation windows 7 and printed conductors including suitable contact surfaces 8 for e.g. a sliding contact arrangement disposed remote from the measuring point are produced.

The next step is used to form an insulating layer 6 on the structured base. For said purpose, use is made of e.g. a mechanical stencil mask, which covers the surface of the shaft 13 apart from the measuring zones and the sliding contact surfaces. An approximately 1.5 m thick high-resistance layer is then applied using the previously described method. The mechanical mask is subsequently removed.

The further layer formation is effected by re-installing the shaft 13 in the e.g. CVD sputtering installation. A DLC layer is then deposited using the previously described method. The thickness of said layer is around 2 m. Instead of the DLC layer, an Me:CH layer may be applied onto the structured W:CH layer. In said case, the resistivity of the layer, which is controlled by means of the Me content, has to be higher than the resistivity of the structured base. Here, therefore, a W:CH layer having a W content of around 5 atom % is advantageously used.

Instead of tungsten, other elements Me may be used for the Me:CH layer, e.g. Ti:CH, Ta:CH, Nb:CH etc.

As already mentioned above, said form of implementation illustrates the local measurement of state variables, here the force, in inaccessible bearings.

Figure 11:
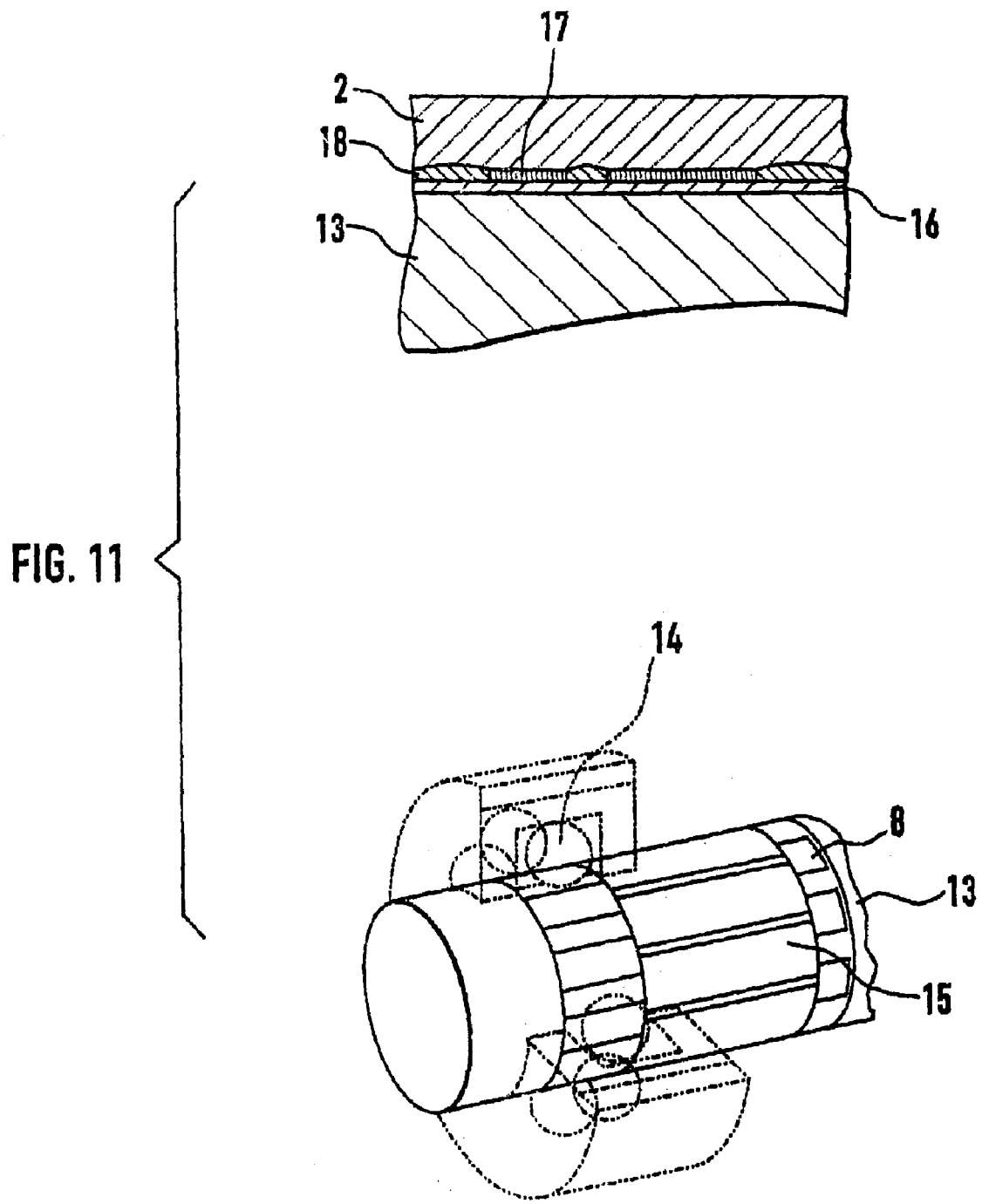

In FIG. 11 the top illustration shows the structure of the layer system according to FIG. 10 and the bottom illustration is a diagrammatic overall view of the bearing illustrated in FIG. 10, with shaft 13, balls/rollers 14 and the structuring 15 for e.g. contacts 8 and printed conductors.

Here, the detail according to the top illustration in FIG. 11 shows the shaft 13, on which a high-resistance layer 16 has been deposited using the previously described method. Situated on said layer is a structured low-resistance Me:CH layer 17 having structures for e.g. contacts and printed conductors as well as a high-resistance layer 18 analogous to the high-resistance layer 17 and, as measuring layer 2, a DLC or Me:CH layer.

Figure 12:
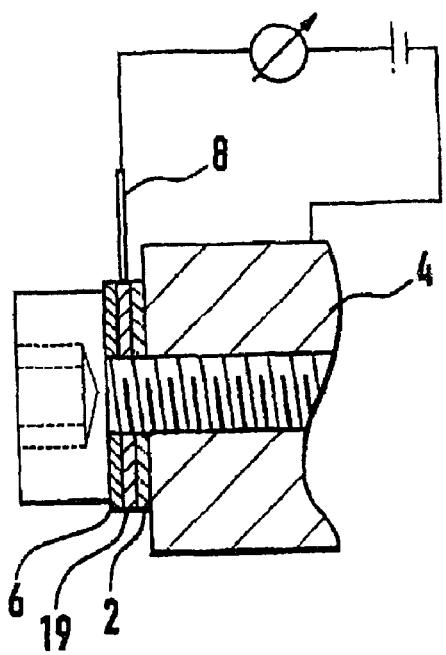

FIG. 12 shows, as a further possible application for the present invention, a washer 19 which has been provided with the measuring layer 2 used according to the invention as a sensor and which may be used to measure and check friction-locked connections. The insulating layer 6 shown here may be e.g. an Si—O—DLC or $Al_2O_3$ layer. As measuring layer 2, again a DLC or Me:CH layer may be used.

Figure 13:
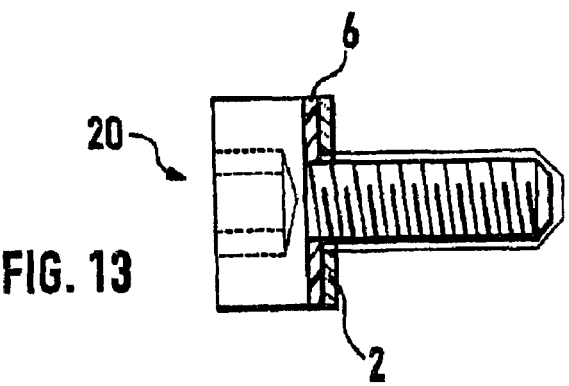

FIG. 13 shows, as a further form of application, a screw head 20, which is provided with the measuring layer 2 used according to the invention as well as with an insulating layer 6.

Figure 14:
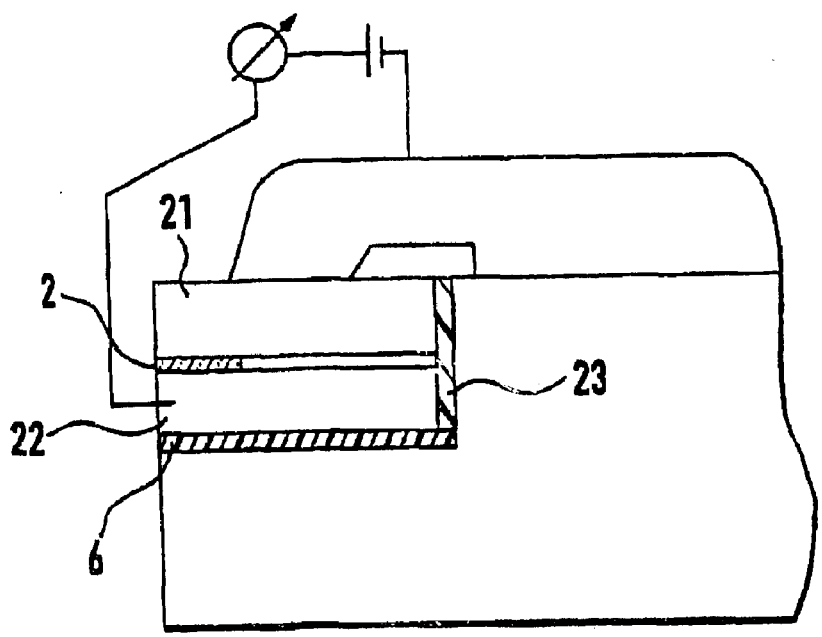

FIG. 14 illustrates the application of the amorphous carbon layer with piezoresistive properties, which is used according to the invention as measuring layer 2, in a turning tool for measuring the chip removing force. Here, a shim 22 (base) is coated with the measuring layer 2. The measuring layer 2 may be applied onto the entire surface or, in an advantageous implementation, alternatively only in one or more separately contactable regions.

The turning tool is equipped with a changeable tool bit 21, an insulating ceramic plate 23 and an insulating layer 6.

As illustrated above by way of numerous examples, the amorphous carbon layer with piezoresistive properties, which is used according to the invention as a sensor for determining state variables such as force or pressure, is versatile and may easily be adapted to the respective requirements of the respective forms of implementation. In said case, the layer may be used as a single layer or as a layer system of any desired configuration. By virtue of the nature and number of the doping elements the respective properties of the layer and/or layer system may be varied in any desired manner.

LIST OF REFERENCE CHARACTERS 1 mechanical component
2 measuring layer (sensor)
3 ram
4 counterpart body
5 circuit
6 insulating layer
7 observation window
8 contact
9 insulating layer for contact
10 main roller
11 contact pressure roller
12 detail of a gearwheel
13 shaft
14 ball/roller
15 structuring
16 high-resistance layer
17 low-resistance layer with structuring for e.g. contacts and printed conductors
18 high-resistance layer
19 washer
20 screw head
21 changeable tool bit
22 base (here, shim)
23 insulated ceramic plate
Legends of FIGS. 1 to 3
Widerstand in Ohm=resistance in ohms
Kraft in N=force in N
Legends of FIG. 4

Widerstand in kOhm=resistance in kOhms
Kraft in N=force in N

What is claimed is:

1. A method of using an amorphous carbon layer with piezoresistive properties as a sensor for measuring actual state variables at a stressed surface of mechanical components, comprising the steps of:
   providing the amorphous carbon layer having piezoresistive properties therein on the stressed surface, the amorphous carbon layer containing a piezoresistive material;
   providing a measuring device coupled to the amorphous carbon layer by an electrical contact; and
   using the amorphous carbon layer as a sensor.

2. The method of use of claim 1, wherein as state variables the force, which is acting upon the surface, and/or the pressure is measured.

3. The method of use of claim 1, wherein the amorphous carbon layer comprises graphitic structures with $sp^2$ hybridization in combination with diamond-like structures with $sp^3$ hybridization.

4. The method of use of claim 1, wherein the amorphous carbon layer is doped with at least one metallic and/or non-metallic element.

5. The method of use of claim 4, wherein the at least one element is selected from Si, Ti, W, Cr, Ta, Nb, V, Zr, Hf, Mo, Pb, Cu, Al, Au, Ag, Pt, Ru, Pd, Ni, Co, oxygen, nitrogen, Ar, F, hydrogen or combinations thereof, in particular from Si, Ti, W and Cr.

6. The method of use of claim 4, wherein the at least one element is contained in the amorphous carbon layer in a quantity of 0.01 to 47 atom %, preferably 1 to 45 atom %.

7. The method of use of claim 1, wherein the amorphous carbon layer is applied as a wear-resistant pressure sensor onto tools and tribologically stressed components.

8. The method of use of claim 1, wherein the amorphous carbon layer is applied as an anti-adhesive pressure sensor onto tools and components.

9. The method of use of claim 1, wherein the amorphous carbon layer is used in combination with further functional layers.

10. The method of use of claim 9, wherein the amorphous carbon layer is an integral layer component in a multilayer system.

11. The method of use of claim 1, wherein the composition of one or more layers varies, in terms of the layer-forming components and/or the concentration of individual layer-forming components, over the layer thickness.

12. The method of use of claim 1, wherein the amorphous carbon layer is constructed as a multi-ply layer system.

13. A method of measuring an actual state variable at a stressed surface of a mechanical component, the method comprising the steps of:
   providing an amorphous carbon piezoeresistive layer having piezoresistive properties within the layer and disposed on the stressed surface;
   providing a measuring device coupled to the amorphous carbon layer by an electrical contact; and
   measuring the actual state variable.

14. The method of claim 13, wherein the pressure/resistance characteristic and/or the resistance level of the amorphous carbon layer is adjusted in dependence upon the content and the nature of the at least one metallic and/or non-metallic element.

15. The method of claim 13, wherein by virtue of additional thermoresistive measurement by a temperature sensor thermal stabilization is effected.

16. A sensor arrangement for measuring actual state variables of a stressed surface of a mechanical component, comprising:
   an amorphous carbon layer overlaying the surface of the mechanical component; and
   an electrical contact coupled to the amorphous carbon layer and to a measuring device;
   wherein the amorphous carbon layer has piezoresistive properties therein.

17. The sensor arrangement of claim 16, further comprising an insulating layer disposed between the amorphous carbon layer and the surface of the mechanical component, wherein the insulating layer is interrupted at least at one point, for measuring the local stress of the mechanical component at said point.

18. A method of using an amorphous carbon layer with piezoresistive properties as a sensor for measuring actual state variables at a stressed surface of mechanical components, comprising the steps of:
   providing the amorphous carbon layer with piezoresistive properties on the stressed surface, the amorphous carbon layer containing a piezoresistive material;
   selecting the amorphous carbon layer from a group of hydrogenated carbon layers (a-C:H) and non-hydrogenated carbon layers (i-c);
   providing a measuring device coupled to the amorphous carbon layer by an electrical contact; and
   using the amorphous carbon layer as a sensor.

19. The method of use of claim 18 wherein the amorphous carbon layer is doped with at least one metallic and/or non-metallic element.

* * * * *